United States Patent
Shakespeare et al.

(10) Patent No.: US 7,695,592 B2
(45) Date of Patent: *Apr. 13, 2010

(54) METHOD AND APPARATUS FOR MEASURING FIBER ORIENTATION OF A MOVING WEB

(75) Inventors: John F. Shakespeare, Kuopio (FI); Markku M. Kellomäki, Kuopio (FI)

(73) Assignee: Honeywell International Inc., Morristown, NJ (US)

(*) Notice: Subject to any disclaimer, the term of this patent is extended or adjusted under 35 U.S.C. 154(b) by 192 days.

This patent is subject to a terminal disclaimer.

(21) Appl. No.: 11/111,584

(22) Filed: Apr. 21, 2005

(65) Prior Publication Data

US 2006/0237156 A1 Oct. 26, 2006

(51) Int. Cl.
D21F 11/00 (2006.01)

(52) U.S. Cl. ............... 162/198; 162/263; 700/122; 700/127

(58) Field of Classification Search ......... 162/198, 162/263, DIG. 11; 356/429–431, 364–368, 356/370, 238.1; 700/122, 127; 250/225, 250/559

See application file for complete search history.

(56) References Cited

U.S. PATENT DOCUMENTS

| | | | |
|---|---|---|---|
| 4,519,041 A | 5/1985 | Fant et al. | 364/552 |
| 4,818,930 A | 4/1989 | Flemming et al. | 324/58.5 |
| 4,879,471 A | 11/1989 | Dahlquist | |
| 4,931,657 A | 6/1990 | Houston et al. | 250/559 |
| 4,955,720 A | 9/1990 | Blecha et al. | |
| 5,094,535 A | 3/1992 | Dahlquist et al. | |
| 5,104,488 A | 4/1992 | Chase | 162/198 |
| 5,138,878 A | 8/1992 | Cresson et al. | 73/159 |
| 5,166,748 A | 11/1992 | Dahlquist et al. | |
| 5,324,475 A | 6/1994 | Okahashi | 264/555 |
| 5,475,233 A | 12/1995 | Fukuoka et al. | |
| 5,581,637 A | 12/1996 | Cass et al. | 382/284 |
| 5,640,244 A | 6/1997 | Hellstrom et al. | 356/429 |
| 5,699,163 A | 12/1997 | Todoroki et al. | 356/445 |
| 5,764,874 A | 6/1998 | White | 396/155 |
| 5,853,543 A | 12/1998 | Hu et al. | |
| 6,059,931 A | 5/2000 | Hu et al. | |
| 6,080,278 A | 6/2000 | Heaven et al. | |
| 6,092,003 A | 7/2000 | Hagart-Alexander et al. | |
| 6,111,651 A | 8/2000 | Shakespeare | 356/429 |
| 6,149,770 A | 11/2000 | Hu et al. | |
| 6,441,904 B1 | 8/2002 | Shakespeare | 356/429 |
| 6,466,839 B1 | 10/2002 | Heaven et al. | |
| 6,606,394 B1 | 8/2003 | Park et al. | 382/108 |
| 6,643,022 B1 | 11/2003 | Komppa | 356/445 |
| 6,717,675 B1 | 4/2004 | Munch | 356/429 |
| 6,799,083 B2 | 9/2004 | Chen et al. | 700/128 |
| 6,805,899 B2 | 10/2004 | MacHattie et al. | |
| 2002/0039181 A1 | 4/2002 | Shakespeare et al. | |
| 2002/0097320 A1 | 7/2002 | Zalis | |
| 2002/0159618 A1 | 10/2002 | Freeman et al. | |
| 2003/0144747 A1 | 7/2003 | Shakespeare | |
| 2003/0156293 A1 | 8/2003 | Kazuhiko et al. | |
| 2004/0037465 A1 | 2/2004 | Krause | |
| 2004/0175043 A1 | 9/2004 | Lee | |
| 2004/0243270 A1 | 12/2004 | Amirthalingam | |
| 2004/0246510 A1 | 12/2004 | Jacobsen et al. | |
| 2005/0004956 A1 | 1/2005 | Pourdeyhimi | |

FOREIGN PATENT DOCUMENTS

| | | |
|---|---|---|
| CA | 2012351 | 9/1990 |
| DE | 34 13 558 C2 | 10/1985 |
| DE | 40 08 366 A1 | 9/1990 |
| EP | 0 612 977 A2 | 8/1994 |
| EP | 1315053 A2 | 5/2003 |

OTHER PUBLICATIONS

Scharcanski J. et al., Texture Analysis for Estimating Spatial Variability and Anisotropy in Planar Stochastic Structures, Optical Engineering Soc., vol. 35, No. 8, 1996.
F. Gadala-Maria et al., Measurement of Fiber Orientation in short-Fiber Composites Using Digital Image Processing, Polymer Composites, vol. 14, No. 2, Apr. 1993.
Scharcanski J. et al., Stochastic Texture Image Estimators for Local Spatial Anisotropy and its Variability, IEEE, vol. 49, No. 5, Oct. 2000.

*Primary Examiner*—Mark Halpern
(74) *Attorney, Agent, or Firm*—Cascio Schmoyer & Zervas

(57) ABSTRACT

An image-based measurement technique that directly measures the orientation of fibers in a moving web that comprises nonwoven material measures the orientation angles of the individual fibers so that a more robust estimate of the statistical distribution of fibers is obtained. The technique includes the steps of: (a) illuminating an area on at least one side of the web with radiation; (b) obtaining at least one digital image of the illuminated area; and (c) calculating the fiber orientation of the web by processing the at least one digital image with a gradient operator thereby analyzing the distribution of observed fiber orientation angles within the image. The gradient operator is preferably of a non-integer order between $\frac{1}{8}$ and $\frac{2}{3}$ and particularly between $\frac{1}{4}$ and $\frac{3}{4}$. The use of fractional-gradient operators yields more reliable results than when integer order gradients are employed.

23 Claims, 8 Drawing Sheets

METHOD AND APPARATUS FOR MEASURING FIBER ORIENTATION OF A MOVING WEB

FIELD OF THE INVENTION

The present invention is directed to techniques of determining the fiber orientation in webs formed from nonwoven materials and particularly to image-based measurements of the average fiber orientation of paper by on-line image analysis.

BACKGROUND OF THE INVENTION

In the manufacture of paper on continuous papermaking machines, a web of paper is formed from an aqueous suspension of fibers (stock) on a traveling mesh, papermaking fabric, or wire and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Papermaking devices well known in the art are described for example in Handbook for Pulp & Paper Technologists 2nd ed., G. A. Smook, 1992, Angus Wilde Publications, Inc., and Pulp and Paper Manufacture Vol III (Papermaking and Paperboard Making), R. MacDonald, ed. 1970, McGraw Hill. Sheetmaking systems are further described, for example, in U.S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al.

In the art of modem high-speed papermaking, it is well known to continuously measure certain properties of the paper material in order to monitor the quality of the finished product. These on-line measurements often include fiber orientation (FO), basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

Fiber orientation in papermaking refers to the preferential orientation of the individual fibers on the web. Because of flow patterns in the headbox and the jet impingement on the wire, fibers have a tendency to align in the machine direction (MD) versus other directions in the web. If all of the fibers in the web were perfectly distributed, the paper sheet would have the same properties in all directions. This is called an isotropic sheet and its fiber distribution can be plotted on a polar graph in the form of a circle. A fiber ratio, which is the ratio of maximum to minimum fiber distribution 90° apart, can be defined for a paper sheet. An isotropic sheet has a fiber ratio of one.

If there are more fibers in one direction than in other directions the fibers are distributed non-uniformly and the sheet is anisotropic. As shown in FIG. 12, the anisotropic fiber distribution can be plotted on a polar graph as a symmetrical ellipse-like geometric 2. An anisotropic sheet has a fiber ratio greater than one and with higher fiber ratios the polar distribution tends to be in the shape of a figure eight. The fiber ratio (anisotropy) is defined as the ratio of maximum to minimum distribution, 90° apart. The fiber angle α is defined as the angle of the major axis 6 of the ellipse 2 to the machine direction 4. The minor axis 8 is perpendicular to the major axis 6. FIG. 12 also illustrates the definitions of FO ratio (the ratio of max 3 to min 5) and FO angle of fiber distribution in a paper sheet. Fiber ratios can also be defined for other orthogonal directions, and it is common in papermaking to use the ratio of the fiber distribution in the machine direction 4 to the fiber distribution in the cross-machine direction 9.

Fiber orientation in formed webs can influence numerous properties of the final product. In particular, if the fiber orientation distribution is incorrect, then dimensional instability in the form of twist, curl, and skew will occur, and strength axes will not correspond to manufacture axes. This leads to defective products such as paper that jams in printers/copiers, packaging that jams in discrete item containers, and boxes which lean or collapse when stacked. By accurately measuring the fiber orientation on-line in the manufacturing process, it is possible to rectify problems in a timely manner either by manual intervention or by a fiber orientation control system.

Numerous techniques for measuring fiber orientation have been suggested some of which are based on the transmission of laser or maser spots from polarized or unpolarized light sources. The distortion of the spot in transmission through the web or the directional variation in intensity of reflection of the illuminated spot, specular or aspecular, is measured. Because the spot illumination area is relatively small, these techniques do not necessarily yield representative measurements for the sheet. Many of these indirect techniques that measure proxies of fiber orientation are based on the physical principle that fibers scatter more light across their alignment direction than along it.

For example, CA 2,012,351 to Karasikov et al. discloses a system for determining fiber orientation in a stationary or moving web of fibers wherein a small circular spot light is focused onto a first surface of the web thereby forming an ellipse-shaped spot on the opposite or second surface of the web. The elliptical light spot is focused onto an array of light-sensitive elements that are positioned parallel and at a predetermined distance on the second surface of the web. The fiber orientation is determined by evaluating the size, orientation and aspect ratio the ellipse-shaped spot to image.

U.S. Pat. No. 4,955,720 to Blecha et al. discloses an on-line method that illuminates on side of a moving sheet with a circular spot of coherent light and acquires a freeze-frame image of the transmitted spot on the opposite side. The fiber orientation angle is estimated from the shape of the transmitted spot, which is presumed to be elliptical.

Similarly, U.S. Patent No. Application 2003/0156293 to Kazuhiko et al. discloses a method that uses an unpolarized focused light beam to illuminate a circular spot on one side of a sheet and images the transmitted spot on the opposite side. Fiber orientation angle and anisotropy are estimated by approximating the transmitted spot shape with an ellipse.

DE 3,413,558 to Hartig describes a technique that employs polarized laser light to illuminate a laser spot on one side of a sheet. Four photodiodes are positioned at the nominal edges of the expected excident spot position along x and y axes on the opposite side. The fiber orientation and anisotropy are determined from the ratio of transmitted intensities summed on each axis. As in the above systems, the Hartig device also measures the total or average fiber orientation in the sheet.

U.S. Pat. No. 5,475,233 to Fukuoka et al., U.S. Pat. No. 5,640,244 to Hellstrom et al., and U.S. Pat. No. 6,643,022 to Komppa disclose various methods in which laser light is obliquely directed onto a sheet and the intensity of aspecularly reflected laser light is measured at various directions and inclination angles. The surface fiber orientation determination is based on the differences in the illumination reflectivity when measured from a number of directions. The methods disclosed differ to some extent in the geometries of the illuminations employed.

Image analysis is a standard laboratory technique for fiber orientation measurements of paper whereby transmission images of stationary sheets taken from flatbed scanners or similar devices are analyzed. Since paper strongly scatters light, the samples usually must be peeled into layers for transmission or reflection imaging to be feasible. The layers typically are very thin and weigh just a few grams per square meter (gsm). This laboratory process is labor-intensive and not applicable to on-line measurements of moving webs.

Therefore, despite the asserted advantages associated with these fiber orientation measurement systems, none of these apparatuses affords a simple, robust, and accurate device for on-line fiber orientation measurements of a moving web or sheet made of nonwoven components.

SUMMARY OF THE INVENTION

The present invention is based in part on the development of an image-based measurement technique that directly measures the orientation of fibers in a moving web that comprises nonwoven material. The technique is capable of measuring a larger area of the web, e.g., paper, than is possible with the spot illumination methods, and thus produces a measurement which is more representative of the web. Moreover, by measuring the orientation angles of the individual fibers, a more robust estimate of the statistical distribution of fibers is obtained.

In one aspect, the invention is directed to a method for measuring the fiber orientation of a moving web that includes the steps of:
  (a) illuminating an area on at least one side of the web with radiation;
  (b) obtaining at least one digital image of the illuminated area; and
  (c) calculating the fiber orientation of the web by processing at least one digital image with a gradient operator thereby analyzing the distribution of observed fiber orientation angles within the image.

In preferred embodiments, each image comprises a plurality of pixels and the gradient operator produces a gradient magnitude and direction for at least one of the pixels. The gradient operator preferably is of a non-integer order between $1/4$ and $3/4$ and particularly between $1/3$ and $2/3$. The use of fractional-gradient operators yields more reliable results than when integer order gradients are employed.

In another aspect, the invention is directed to a system for measuring the fiber orientation of a moving web that includes:
  image obtaining means for obtaining at least one digital image of an illuminated area on the moving web; and
  control means for calculating the fiber orientation of the web by processing the at least one digital image with a gradient operator.

The image-based measurement technique is particularly suited for incorporation into a continuous web production process, such as for making paper, where the fiber orientation of the moving web is monitored. Images of the moving web can be ascertained at one or more fixed positions relative to the moving web either in the machine direction or cross direction. Images can also be ascertained as a image detector scans back-and-forth typically in the cross direction across the moving web. For example, the image detector can be mounted on a traversing sensor platform so that the full width of the web is sequentially measured. Moreover, the invention can be used to measure the fiber orientation in the forming section of the process, so that the fiber orientation can be measured for each layer of a multi-layer web, before the layers are spliced together. This allows the fiber orientation to be known in the interior as well as at the surface of a multi-layer web.

The image-based measurement technique does not require measuring an indirect proxy of fiber orientation as in the prior art nor does it employ spot or laser illumination. Furthermore, it does not rely on the distortion of a spot in transmission through the web nor on directional variation in intensity of reflection of an illuminated spot, specular or aspecular.

DETAILED DESCRIPTION OF THE PREFERRED EMBODIMENTS

Figure 1:
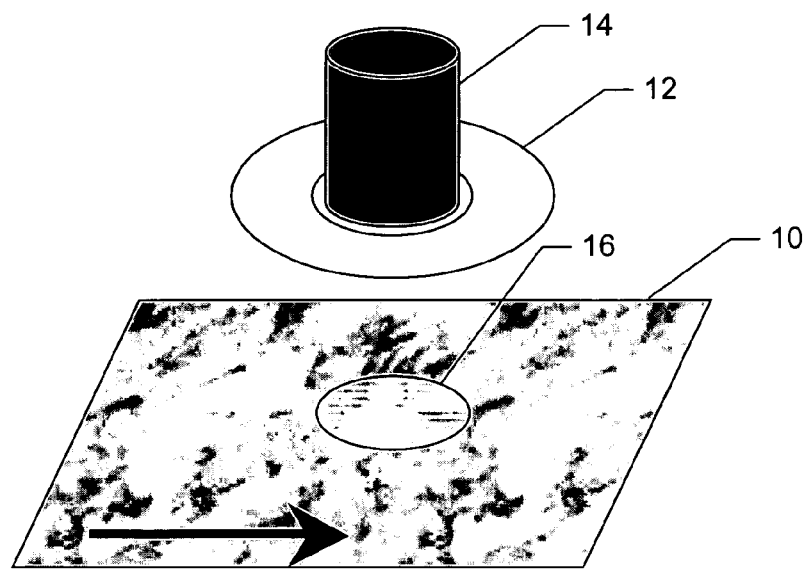
FIG. 1 illustrates fiber orientation measurements by on-line image analysis whereby the illumination source and imaging device are positioned on the same side of the moving web.

The present invention relates to methods and devices for directly measuring the fiber orientation in nonwoven materials especially where the material is in the form of a moving web, film or sheet. The fiber orientation of the whole thickness of the web or just the surface of the web can be measured. The fiber orientation measurements can be expressed as one or more different parameters that are used in controlling the papermaking process and/or characterizing the properties of the product. The parameters include, for instance: average fiber orientation angle, fiber orientation anisotropy index, and statistical distribution of fiber orientation angles. In addition, the fiber orientation measurements from both sides of the web can yield information regarding curl and twist deformations of the web, e.g., paper.

The analysis method employs fractional-order gradients that are evaluated on at least two preferably orthogonal axes at a plurality of loci in the digital images obtained of a web being monitored. The evaluation loci preferably essentially cover an image of at least 10 mm in sheet width. Preferably, the fractional-order gradients are averaged or smoothed over small scales. A characteristic angle is formed from the at least two fractional gradients at each evaluation locus, for instance, by taking the arctangent of their ratio. The distribution of angles can then be characterized in various ways, such as by evaluating an average angle, or by fitting the distribution of angles to a specified parametric form.

If the digital image has blurring of features in the direction of movement of the web, a preprocessing procedure is preferably executed before the image is analyzed. For instance, a compensating blurring operation can be carried out in the orthogonal direction, but a deblurring or sharpening could be carried out in the direction of blur in some cases. If the web is non-opaque and there is a pattern in the background or if the web is transported on a forming fabric or other textured background, then the estimation of angles can be modified. This is important if the background texture is directional, such as for the forming fabrics in the fourdrinier section of a paper machine. For instance, the angles corresponding to those dominant in the background can be omitted from analysis when estimating the average angle or parameters of a distribution. Preferably, the background can be measured without the web, so that its characteristics can be determined.

While the invention will be illustrated in measuring fiber orientation of paper, it is understood that the invention can be employed to analyze fiber orientation in a variety of products that are formed from non-woven fibrous materials including, for example, paperboard, tissue and the like. In addition, the invention has applicability outside products that are derived from cellulose. For instance, the measurement techniques can be applied in the manufacture of glass fiber sheets in which the control of fiber orientation distributions is also critical.

As shown in FIG. 1, an apparatus for measuring fiber orientation of a moving web 10 or sheet of paper includes an imaging device 14 and an annular light source 12 that are both positioned above the web 10. The imaging device 14 is typically a camera that is equipped with appropriate optics, e.g., lenses, to focus light that is reflected from the image area 16 into the camera. In this reflective mode configuration, surface images of the moving web 10 are derived from light that is reflected from the surface. The reflective mode of operation is particularly suited for measuring fiber orientation of web comprising a layer of opaque material or a web that is supported underneath by a fabric, wire or other structure that interferes with the transmission of light. Light from the light source 12 is directed toward the web 10 to illuminate an area on the surface and the imaging device 14 detects images from an image area 16 which is within the illuminated area. Although the size of the lumination area is not critical, it preferably is large enough to permit the imaging device 14 to image an area 16 that is at least about 25 $mm^2$ and is typically from 100 $mm^2$ to 1000 $mm^2$ in size. As is apparent, the larger the image area 16 on the web, the more representative is the fiber orientation that is measured.

The imaging device 14 and light source 12 are configured so that the image scale is sufficient to allow fibers in the moving web 10 to be discerned. Thus, imaging detectors, e.g., cameras, suitable for use as the imaging device 14 should have pixel sizes that do not exceed the typical width of a single fiber. This corresponds to about 20-40 microns per pixel in the imaging detector when using adequate lenses. The digital images formed are analyzed using gradient-type operators in two preferably orthogonal directions. It is not necessary to analyze every pixel in the image, and it is preferable to analyze a subset which represents a disk of at least a centimeter in diameter on the paper, or a random sample of such a disk.

Conventional lenses can be employed with the camera when the moving web 10 is stable so that its distance from the imaging device 14 is relatively constant which is the case when the web 10 is adequately supported. However, if aerodynamic effects cause the moving web 10 to flutter or otherwise shift its vertical position relative to the imaging device 14, a telecentric lens system that creates a large depth of field can be used so that fluctuations of the web 10 relative to the camera results in no change in image size.

When the light source 12 is located on the same side as the imaging device 14 as shown in FIG. 1, the illumination is preferably symmetrical around the optical axis of the imaging device 14. For instance, an annular-shaped light source 12 where the illumination from the light source 12 to the web 10 is directional, typically at an angle that is from about 30° to 75° to normal, can be employed. Light sources that produce illumination having angles outside this range can also be used, but less uniform image weighing to each fiber direction is achieved. Alternatively, light sources that generate multiple beams of light with multiple angles of illumination can be employed. As further described herein, the illumination can be derived from an array of light sources that are distributed in one or more concentric annuli such that the illumination is substantially symmetrical around their common axis. Different light beams can be directed at the web 10 either simultaneously or sequentially. The illumination can be monochrome or polychrome and the character of illumination can differ between illumination angles. Although the wavelength of the radiation is not critical, ultraviolet, visible, and especially near-infrared radiation are preferred for measuring fiber orientation in paper.

In the case where the web of material being monitored contains an appreciable amount of water or non-fibrous material such as resins, fillers or sizing starch, imaging at different wavelength ranges can allow for better discrimination between the fibrous and non-fibrous materials. The apparatus can comprise a light source 12 such a quartz tungsten halogen (QTH) lamp that supplies a broadband infrared radiation and one or more detectors with the wavelength of interest being selected by a narrow-band filter, for example, an interference type filter. The images can be obtained, for instance, by prismatic or partial-mirror separation into multiple images of the same illuminated area. In particular, fluorescence can be advantageously used, whereby the wavelength range of measurement for one image is in the fluorescence emission band, and illumination is at low intensity in that band, but high intensity in the fluorescence excitation band.

The concept is to take advantage of fluorescent agents already present in some paper for any of several purposes: (i) to help distinguish between fiber and non-fiber constituents, (ii) to help distinguish between surface and subsurface fibers, or (iii) to boost the amount of light which forms the image on the detector. It is understood that a fluorescent agent can be added explicitly to facilitate measurement.

Many grades of paper include fluorescent agents to enhance their perceived color. For example, fluorescent brightening agents (such as Tinopal (UP) are usually present in office paper, e.g., photocopy/laser/inkjet, and are often used in other white grades. The excitation band for these agents is typically from 330 nm to 410 nm with emission from 380 nm to 500 nm. Thus they boost the blue content of remitted light when the illumination contains some ultraviolet. This makes the paper appear brighter as the remitted light is boosted overall, and makes it look whiter as it counters the intrinsic yellow cast of lignin in cellulose fibers which have not been completely bleached.

Some specialty grades use other fluorescent agents. For example, very intense colors can be achieved by using fluorescent dyes. These work in a similar fashion to fluorescent brighteners, except that the fluorescent excitation and emission bands are shifted. For example, Fastusol Yellow 14L has fluorescent excitation in blue centered at 450 nm and emission in green centered at 510 nm. Fluorescent agents having particular excitation and emission behavior are often used in security papers, such as currency or other financial instruments, and in stock certificates, commercial bonds, etc.

Fluorescent brightening agents are normally dosed into the stock stream and are thus adsorbed onto the fibers before filler material is introduced. If the paper is illuminated primarily with ultraviolet (UV-A), then an image formed using blue light will be predominantly fluorescent emission from the fibers. The fillers may absorb or scatter the ultraviolet light, but they will not contribute much to the fluorescent emission in blue.

In a multilayer sheet, fluorescent brightening agents are introduced mostly into the surface layers. This is where they have the most effect, and since they tend to be expensive, dosing them into the interior layers would not be economic. Even in a single layer sheet, ultraviolet light tends to penetrate less into the sheet than visible light, due to scattering effects. Thus, the fiber orientation inferred from a visible light image formed with visible light illumination, and the fiber orientation inferred from a blue light image formed with ultraviolet illumination may differ. The difference is in part due to the difference in orientation of interior fibers compared to surface fibers.

If the sheet is illuminated with a rich light source, i.e., one which includes both UV and visible light, then fluorescence will boost the intensity of an image received by a detector sensitive to visible light.

Diffuse illumination can also be used, especially if aerodynamic effects are small and the web 10 does not flutter. Diffusion illumination can be created by positioning a diffuser in the light path. Diffuse lighting can be created by reflecting light from a light source off one or more reflective surfaces that provide for non-directional and softer illumination.

The light source 12 preferably provides high intensity illumination that consists of a constant stream of energy within a wavelength required for measurement. The light source 12 can be amplitude modulated by conventional mechanical devices such as choppers, shutters, tuning forks and the like to enhance the signal-to-noise ratio. Another exemplary modulating technique employs electro-optical shutters such as Kerr cells and Pockels cells that are positioned in the light beam path of the light source and acousto-optical devices such as acousto-optical tunable filters. Alternatively, direct modulation of a drive current that is coupled to the light source to generate pulsed illumination can be used.

Preferred light source devices include light-emitting diode (LED), laser diode, or an array of LEDs or laser diodes. When the light source is modulated to create a stroboscopic flash effect, for instance, a high modulation rate is preferred. The resulting short exposure times allow the imaging device 14, with correspondingly short integration times, to obtain better images of the image area 16 by reducing or eliminating the adverse effects caused by motion-blurring in the direction of movement of the web 10. In the case of a charge-coupled device (CCD), a short integration time lets pixels collect less light and a longer integration time lets pixels collect more light. Alternatively, or in addition to modulating the light source, the imaging device 14, e.g., CCD camera, that operates at a high exposure rates, i.e., short integration times, can be selected. In this case, the illumination can be continuous which makes it is easier to maintain consistent illumination at different measurements.

Figure 2:
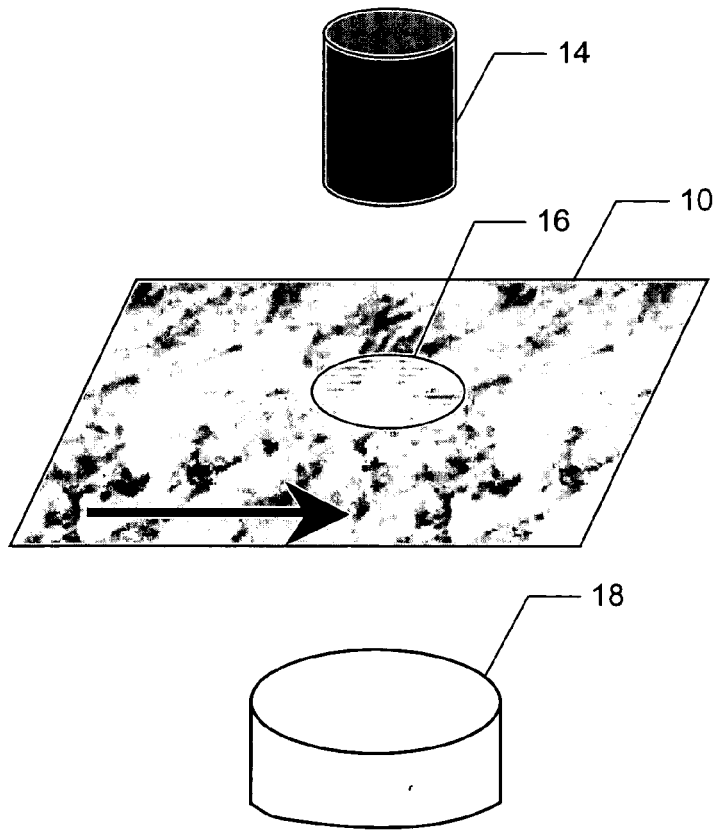
FIG. 2 illustrates fiber orientation measurements by on-line image analysis whereby the illumination source and imaging device are positioned on opposite sides of the moving web.

FIG. 2 illustrates the transmissive mode of operation for measuring fiber orientation of a moving web 10 or sheet of paper. This configuration is particularly suited for monitoring an unsupported, non-opaque web. Indeed, when the web is non-opaque and is not supported by a wire or other structure, both reflective and transmission modes of operation can be employed. As illustrated in FIG. 2, the apparatus includes a light source 18 and imaging device 14 that are positioned on opposite sides of the web 10. The intensity of the light from the light source 18 must be high enough to transmit through the thickness of the web 10 to illuminate the upper surface of the web 10 for images of the image area 16 to be focused into the imaging device 14, e.g., camera. The light source 18 can be positioned directly below the imaging device to provide directional illumination that is perpendicular to the web. Alternatively, the light source 18 can have an annular shape or other configuration for directional illumination that is symmetric around the optical axis of the imaging device 14. In the transmissive mode of operation, the intensity of the illumination can be adjusted so that image captured by the imaging device 14 represents the fiber orientation at different depths in the web.

Figure 3:
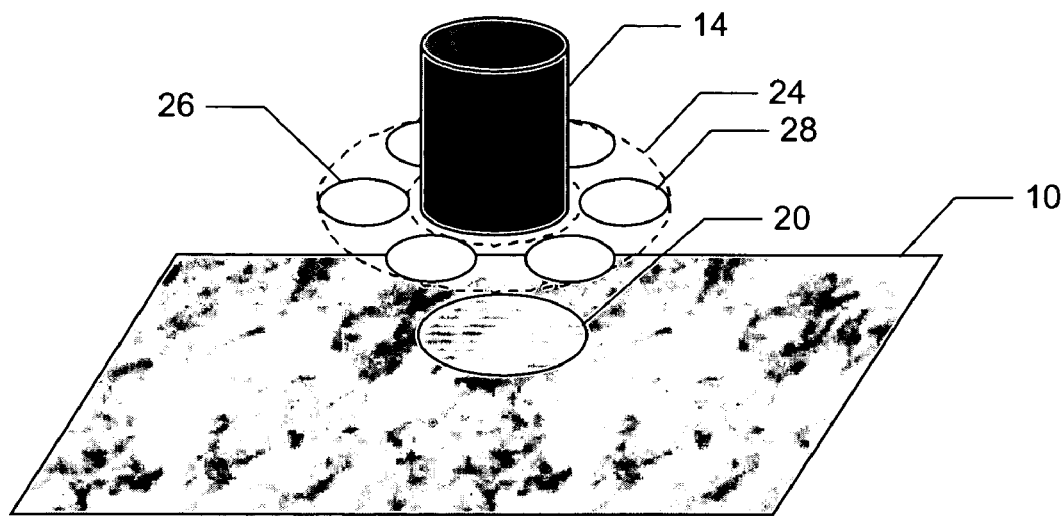
FIGS. 3 and 4 illustrate fiber orientation measurements by on-line image analysis whereby the illumination is an annulus of light sources which is on the same side of the moving web as the imaging device.

FIG. 3 illustrates another reflective mode configuration for fiber orientation measurements of a moving web 10 that includes an imaging device 14 and an annular light source 24 that illuminates area 20 on the web 10. The light source 24 includes a set of light sources 24, 26, and 28, for example, that are distributed along a concentric annulus such that the directional illumination is substantially symmetrical around the axis.

Figure 4:
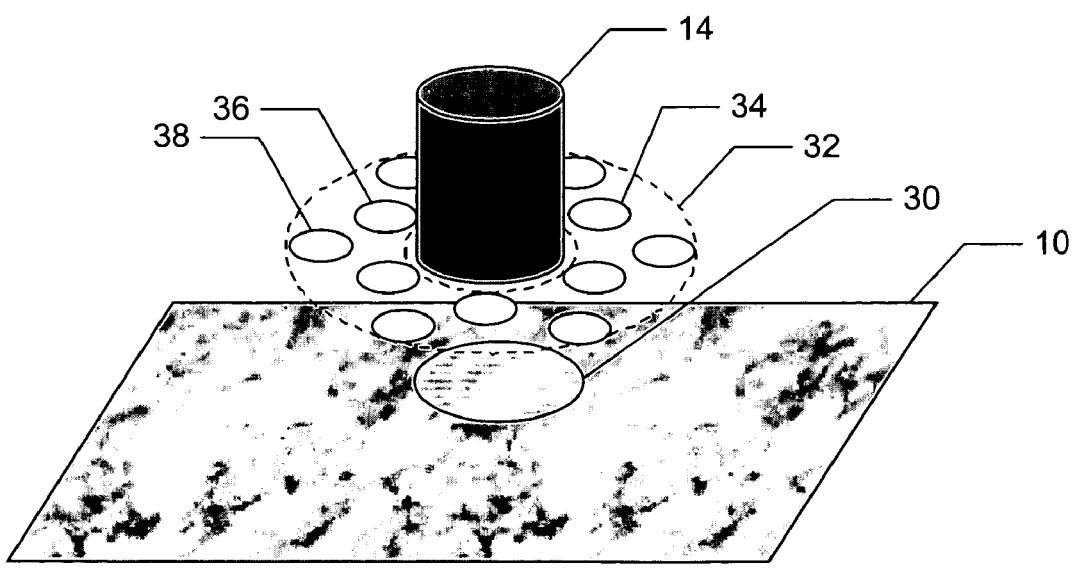

FIG. 4 illustrates a further reflection mode configuration for fiber orientation measurements of a moving web 10 that includes imaging device 14 and an annular light source 32 that illuminates area 30 on the web 10. The light source includes a set of light sources 34, 36, and 38, for example, that are distributed in two concentric annuli such that the directional illumination is substantially symmetrical around their common axis.

Figure 5:
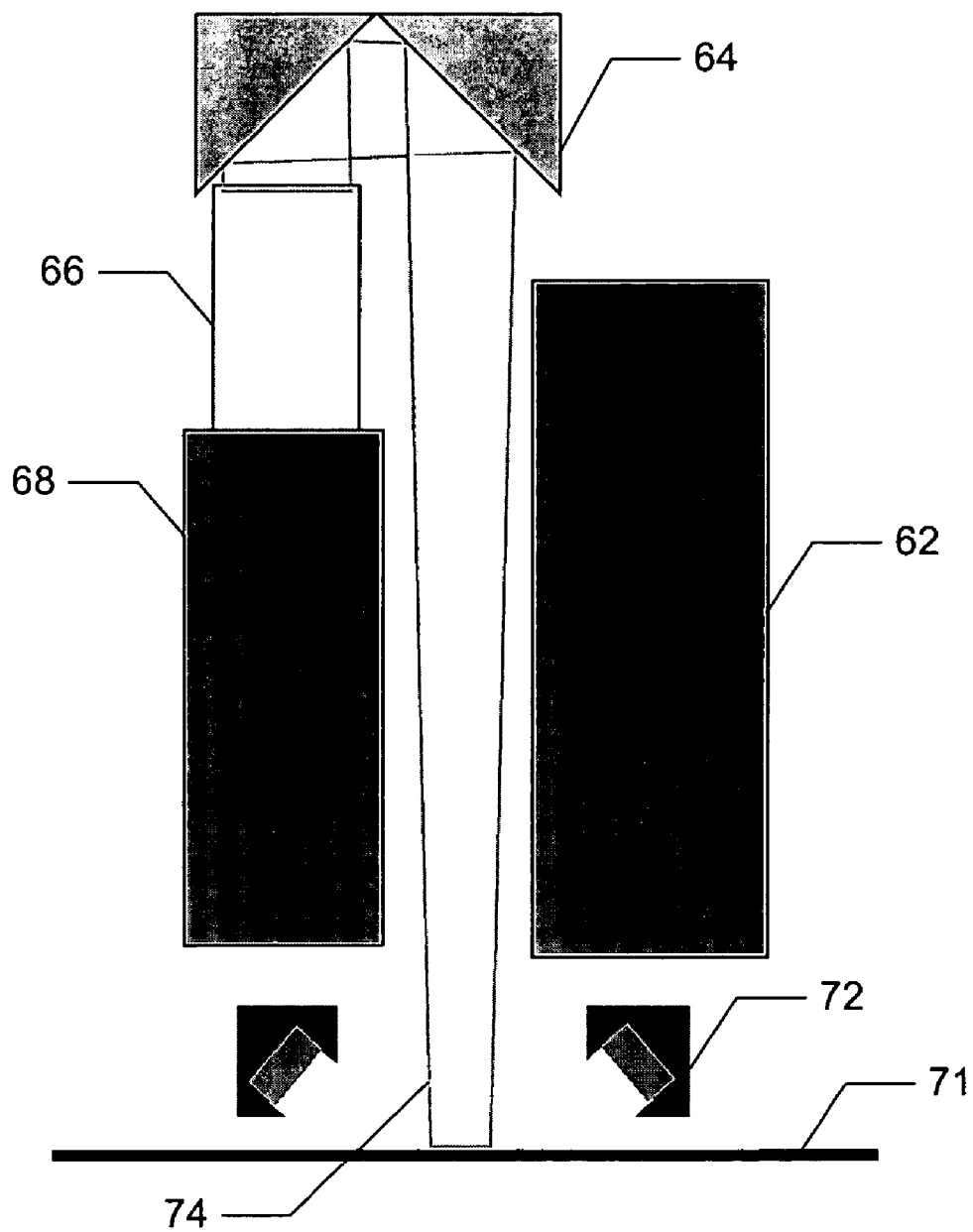
FIGS. 5 and 6 illustrate two embodiments of the inventive apparatus.

FIG. 5 is the cross sectional view of an apparatus for fiber orientation measurements operating in the reflective mode. The light source 72 is a LED ringlight that is positioned about 10 mm from the moving paper 71. A DC LED strobe controller 62 controls the light source 72 to generate strobing illumination for imaging the fast-moving web 71. A suitable strobe controller is the model S4000 by Advanced Illumination (Rochester, Vt.). A camera 68 is a charge-coupled device model XCD-X710 from Sony Corp. (New York, N.Y.). Light 74 reflecting from the paper 71 is directed by optically flat mirrors 64 into a very high resolution 50 mm lens 66 that is coupled to the camera 68. In one embodiment, the optics is configured so that the camera focuses down on an illumination spot on the surface of the web that is 10 to 15 mm in diameter.

Figure 6:
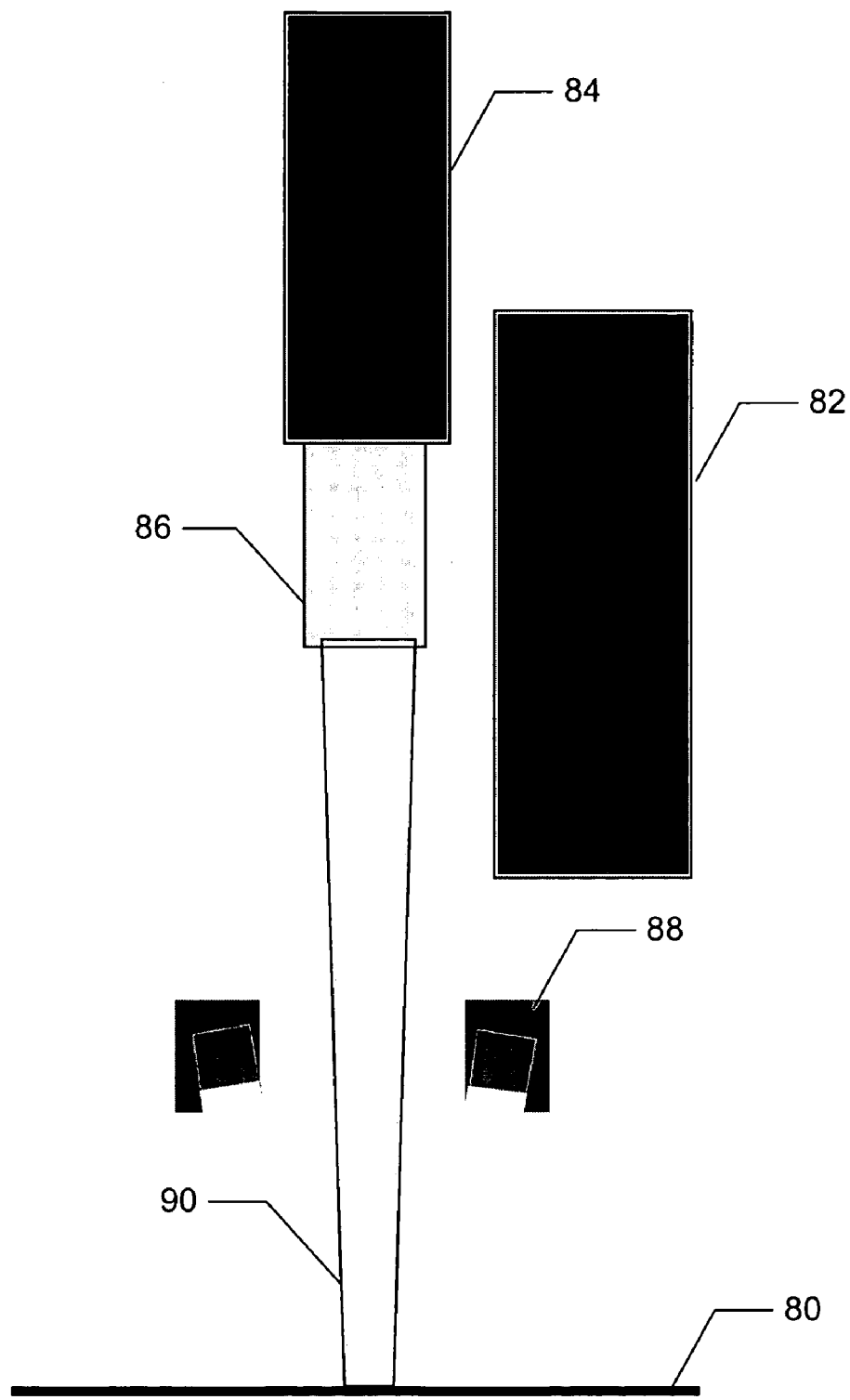

FIG. 6 is the cross sectional view of another apparatus for fiber orientation measurements operating in reflection mode. The light source 88 is a LED ringlight that is positioned about 75 mm from the moving paper 80. A DC LED strobe controller 82 controls the light source 88 to generate strobing illumination for imaging the fast-moving web 80. Light 90 reflecting from the paper 80 is captured by a charge-coupled device camera 84 through a very high resolution 50 mm lens.

Figure 7:
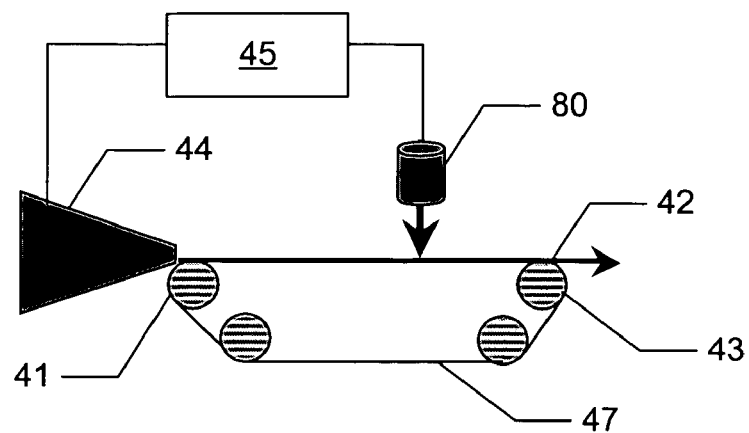
FIGS. 7, 8, and 9 depict various deployments of the inventive fiber orientation measurement apparatus.

The invention can be used to measure the fiber orientation at strategic locations throughout the papermaking process. FIG. 7 shows a portion of a typical sheetmaking system for producing a continuous sheet of paper material 42 that has a plurality of actuators that are arranged to control discharge of wet stock from a headbox 44 onto a supporting fourdrinier wire 47 along the cross direction (CD) which is transverse to the machine direction (MD) of the moving paper material 42. The paper material 42, which is a sheet of fibrous slurry that forms on top of the wire 47, is trained to travel in the MD between the rollers 41 and 43 and thereafter passes through a calendaring stack (not shown). The portion of the papermaking process near the headbox 44 is commonly referred to as the "wet end," while the portion of the process near a take-up reel is referred to as the "dry end". As illustrated, the imaging device and light source components of the inventive apparatus, which are collectively depicted as device 80, are deployed in the reflective mode above the forming unit and after partial dewatering of the slurry, that is, after the jet impingement region.

One of the advantages of the present invention is that it can be employed to measure the fiber orientation at the forming section of at the fourdrinier of a paper or paperboard machine as shown in FIG. 7. This is especially beneficial if multiple plies are spliced together after formation to form a multiply product. The invention allows independent measurement and control of the fiber orientation in each ply. Eliminating or reducing the degree of differences in fiber orientation between plies, results in better products with fewer twist and curl deformations. These deformations are known to cause dimensional instability in folding boxboard or detachment of fluting from liners in corrugated boards.

The inventive fiber orientation measurement apparatus further includes a computer 45 that is connected to an imaging device component of device 80 and actuators of the headbox 44. The computer 45 analyzes the digital images from the imaging device to estimate the fiber orientation of the paper 42 as further discussed herein. In addition, the computer includes a profile analyzer which includes a control system that operates in response to the cross-directional measurements from device 80. In operation, device 80 can be scanned in the cross direction to provide the computer 45 with digital images of the paper along the cross direction. From these images, signals that are indicative the fiber orientation at various cross-directional measurement points are generated. The profile analyzer also include software for controlling the operation of various components of the sheetmaking system, including, for example, the above described actuators of the headbox 44. Depending on the degree of deviation of the fiber orientation from a desired set point, wet end and/or dry end parameters can be adjusted accordingly to change the fiber orientation.

For example, the fiber orientation profile in paper can be altered by distorting the shape of the headbox slice lip or by changing the inlet flow profile from a manifold to the headbox. In both cases, the velocity field of the jet of slurry to the wire is altered, such that the fiber orientation profile and other properties of the paper are changed. Thus, multiple parameters, e.g., slice lip configuration and manifold inlet flow profile, can be manipulated in order to control the fiber orientation of a web.

As is apparent, the present invention provides a method of on-line measuring the fiber orientation of a moving web by analyzing digital images thereof. Empirical data derived from this technique can be employed for process modeling, simulation and control of a sheetmaking system for making products comprising nonwoven materials. A method of developing a mathematical model is to stimulate or perturb the sheetmaking process and measuring the responses, i.e., changes in the fiber orientation, if any, that result. For example, the slice lip and/or manifold can be manipulated at different levels and the responses measured. The mathematical models can be used to regulate the system in order to control the fiber orientation of the sheet. Process control techniques for papermaking machines are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et. al, U.S. Pat. No. 6,080,278 to Heaven et al., U.S. Pat. No. 6,059,931 to Hu et al., U.S. Pat. No. 5,853,543 to Hu et al., and U.S. Pat. No. 5,892,679 to He, which are all incorporated herein by reference.

Figure 8:
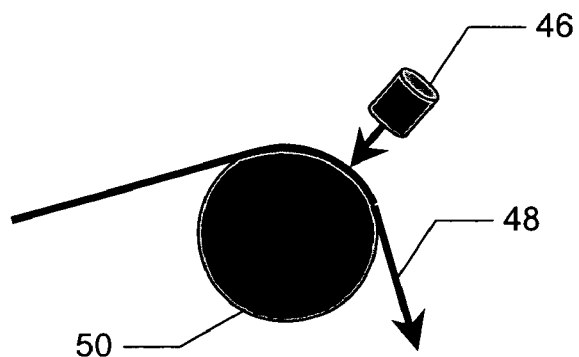

FIG. 8 illustrates the inventive apparatus 46, which is configured to operate in the reflective mode, being deployed to measure the fiber orientation of paper 48 as it moves over a rotation support 50 which can be a roller, dryer cylinder, and the like. If the rotation support 50 is made of at least partially transparent material then the apparatus 46 can operate in the transmissive mode with a light source on one side of the paper and an imaging device on the other, e.g., located within the rotation support 50.

Figure 9:
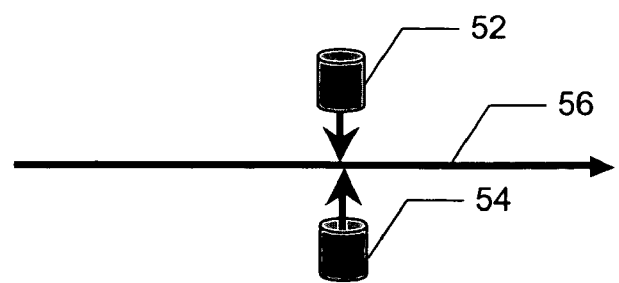

FIG. 9 illustrates an embodiment where both the reflective and transmissive modes of operation can be used to measure the fiber orientation on both sides of a web 56 which is positionally constrained to travel in a relatively straight line without much fluttering, for instance, by tension or aerodynamics. In this case, both the upper and lower sides of the web are illuminated and/or imaged by device 52 and 54, respectively. Where the web can be transported unsupported, as at the dry end of a paper machine, both sides of the web can be measured simultaneously. If the unsupported web is opaque or nearly opaque, then the two sides of the web can be measured independently with two separate apparatuses 52 and 54 each operating in the reflective mode.

On the other hand, if the unsupported web is transparent or only partly opaque, measurement of both sides can be accomplished by employing two separate apparatuses 52 and 54 each operating in the reflective mode. Alternatively, the measurement of both sides can be accomplished by employing two separate apparatuses 52 and 54 each operating in the transmissive mode or the measurement of both sides can be accomplished by employing two separate apparatuses 52 and 54 one operating in the reflective mode and the other in the transmissive mode. Finally, the measurement of both sides can be accomplished by employing two separate apparatuses 52 and 54 one operating in the reflective mode and the other in the transmissive mode with the proviso that illumination is directed from only on side of the web.

The fiber orientation of a moving web can be monitored both in the cross direction and the machine direction. In the latter scenario, multiple apparatus can be positioned in tandem in the MD along suitable positions of a papermaking machine to optimize papermaking machines. A continuous fiber orientation profile of the paper stock on the web can be generated compared to an "ideal" profile for making a particular grade of paper. Depending on the degree of deviation from ideal, wet end and/or dry end parameters can be adjusted accordingly. See, for example, U.S. Pat. No. 6,092,003 to Hagart-Alexander which is incorporated herein.

Similarly, for CD measurements, an array of apparatuses can be positioned along the CD at any suitable position of the papermaking machine. Alternatively, a scanning system that includes single apparatus that is scanned across the width of a web can be employed. Scanner systems generally includes pairs of horizontally extending guide tracks that span the width of the paper product to be monitored. The sensor is secured to a carriage that moves back-and-forth over to paper product as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein by reference.

The configuration as illustrated in FIG. 9, which employs both reflective and transmissive modes of operation, is particularly suited for measuring the topside and bottomside fiber orientations both in the CD and MD of paper. Fiber orientation profiles can be produced simultaneously. These measurements are directly or indirectly linked to other sheet properties like strength and/or web tension and/or shrinkage and elongation and/or sheet curl and twist. By making calibration fiber orientation measurements using paper having known sheet properties, a library of can be established to correlate fiber orientation measurements to actual strength, web tension, shrinkage, twist or curl, and other characteristics.

The image-based measurement technique of the present invention estimates fiber orientation by analyzing digital images using gradient-type operators in two preferably orthogonal directions. The following summarizes some salient results from a field of mathematics, namely the fractional calculus, which unifies differentiation and integration as a singe operation termed differintegration, and encompasses non-integer orders of differentiation and integration. The theory and methods of the fractional calculus are described, for example, in K. Oldham and J. Spanier, "The Fractional Calculus", Academic Press 1974, which is incorporated herein by reference.

Analytically, differintegration can be expressed concisely in integral transform function spaces. For example, let the Laplace transform of a function $f(x)$ be denoted $F(s)$, where $s$ is the Laplace space parameter denoting the transformation of the variable $x$, and let the symbol L denote taking the transformation. Thus:

$$L\{f(x)\} = F(s) = \int_{-\infty}^{+\infty} e^{-sx} f(x) dx. \quad (1)$$

Differintegration of a function to order q with respect to x corresponds to multiplication of its transform by the transform parameter s raised to the q-th power:

$$L\left\{\frac{d^q}{d(x-a)^q} f(x)\right\} = s^q F(s). \quad (2)$$

Thus, as is apparent differintegration to a fractional order cannot be adequately represented as a combination of conventional differentiations or integrations to integer orders, and is a distinct operation. For example the semiderivative cannot be construed as a linear combination of the function and its derivative, any more than $s^{1/2}$ can be approximated as a combination of 1 and s.

While useful in symbolic mathematical analysis, the Laplace transform and other integral transform operators are unwieldy in practical numerical analysis of measured data. However, several formulations of generalized differintegration are mathematically equivalent and may be employed to construct a variety of algorithms for numerical differintegration. For instance, the Grünwald formulation defines the generalized differintegral of order q of a differintegrable function $f(x)$ as:

$$\frac{d^q}{d(x-a)^q} f(x) = \lim_{N \to \infty} \left\{ \frac{\left(\frac{x-a}{N}\right)^{-q}}{\Gamma(-q)} \sum_{k=0}^{N-1} \frac{\Gamma(k-q)}{\Gamma(k+1)} f\left(x - k\left(\frac{x-a}{N}\right)\right) \right\} \quad (3)$$

which in the limit relies on all values of the function in the interval from a to x. With q=1, and with a arbitrarily close to x, this yields the conventional derivative. With q=−1, it yields the conventional antiderivative (often termed the "indefinite integral") or the conventional integral (often termed the "definite integral"), depending on the choice of values for a and x.

The definition (Eq. 3) is valid and forms a numerically convergent series for all differintegrable functions of real, complex, or quaternion numbers (including discontinuous functions, provided they are finite). It also converges for arbitrary values of q, including complex and quaternion values of q. Other formulations of differintegration include those of Riemann, Liouville, Weyl, Heaviside, and Civin, among others. Some of these formulations are confined to specific situations, such as applying only to periodic functions. The Grünwald formulation is the most general and the Riemann-Liouville formulation is the next most general (it converges only when the real part of q is negative and requires analytic continuation with repeated conventional differentiation when the real part of q is positive, restricting it in these cases to continuous functions).

A number of numerical algorithms for performing differentiation to non-integer order are available; they present algorithms based on the Riemann-Liouville formulation as well as on the Grünwald formulation. A preferred algorithm is the Grünwald formulation as it directly yields convolutions of finite length for differintegration when the real part of the order is strictly positive. Of course other formulations can be used instead, if desired.

By omitting the limit in (3) and truncating the series to a finite number of terms N+1, with a fixed interval h between abscissae at which the function $f(\cdot)$ is known, an approximation for the differintegral of order q is obtained. For convenience and without loss of generality, we can set a=x−Nh, yielding:

$$\left(\frac{d^q}{dx^q}\right)_{-} f(x) = \frac{h^{-q}}{\Gamma(-q)} \sum_{k=0}^{N} \frac{\Gamma(k-q)}{\Gamma(k+1)} f(x - kh) \quad (4)$$

The weight factors applied to the function on the right hand side of (4) can be used as the convolution kernel in a convolution representation of differintegration, or as elements of a row in a matrix representation of differintegration. Note that although the gamma function $\Gamma(k-q)$ is unbounded when k−q is a negative integer, the ratio $\Gamma(k-q)/\Gamma(-q)$ is always finite, and can be computed using Stirling numbers of the first kind. The negative subscript on the operator on the left hand side of (Eq. 4) denotes that the expression on the right hand side is a backward-difference approximation to the differintegral at x, since it does not employ any function values at abscissae greater than x. However, a forward difference approximation can also be constructed from Eq. 3 with equal validity by reversing the sense of the interval [a,x], so that a=x+Nh before simplifying:

$$\left(\frac{d^q}{dx^q}\right)_+ f(x) = -\frac{h^{-q}}{\Gamma(-q)} \sum_{k=0}^{N} \frac{\Gamma(k-q)}{\Gamma(k+1)} f(x+kh) \quad (5)$$

The positive subscript on the operator on the left hand side of (Eq. 5) denotes that the expression on the right hand side is a forward-difference approximation to the differintegral at x, since it does not employ any function values at abscissae less than x. The negation on the right-hand-side corrects for the change in direction of the differintegration. A centered difference approximation can be obtained by combining the forward difference and backward difference expressions. Thus, the convolution weights $w_k$ for a centered difference approximation to a differintegral of order q with 2N+1 terms are generated as:

$$w_k = \begin{cases} \dfrac{-h^{-q}\Gamma(-k-q)}{2\Gamma(-q)\Gamma(1-k)} & k < 0 \\ 0 & k = 0 \\ \dfrac{h^{-q}\Gamma(k-q)}{2\Gamma(-q)\Gamma(k+1)} & k > 0 \end{cases} \quad (6)$$

For example, with h=1, convolution kernels of 9 terms derived from (Eq. 6) using N=4 giving centered approximations to some differintegrals of fractional order not exceeding unity are (neglecting a factor of ½ for clarity):

| Order q | $w_{-4}$ | $w_{-3}$ | $w_{-2}$ | $w_{-1}$ |
|---|---|---|---|---|
| ¼ | +3177/2048 | +317/128 | +313/32 | +311/4 |
| ⅓ | +3110/243 | +315/81 | +311/9 | +311/3 |
| ½ | +315/128 | +311/16 | +311/8 | +311/2 |
| ⅔ | +317/243 | +314/81 | +311/9 | +312/3 |
| ¾ | +3145/2048 | +315/128 | +313/32 | +313/4 |
| 1 | 0 | 0 | 0 | −1 |

| Order q | $w_0$ | $w_1$ | $w_2$ | $w_3$ | $w_4$ |
|---|---|---|---|---|---|
| ¼ | 0 | ¼ | 3/32 | 7/128 | 77/2048 |
| ⅓ | 0 | ⅓ | 1/9 | 5/81 | 10/243 |
| ½ | 0 | ½ | 1/8 | 1/16 | 5/128 |
| ⅔ | 0 | ⅔ | 1/9 | 4/81 | 7/243 |
| ¾ | 0 | ¾ | 3/32 | 5/128 | 45/2048 |
| 1 | 0 | 1 | 0 | 0 | 0 |

It can be seen that successive terms at either end of the kernel are declining in magnitude and that they decline less rapidly for orders closer to zero than for orders closer to unity (this observation cannot be generalized to orders of zero or less, or greater than unity). Also, the first term on either side of the center is equal in magnitude to the order of the differintegral, and thus is greater for orders close to unity than for orders close to zero, so that the significance of subsequent terms declines quite rapidly for orders above ½. For most purposes, a five term approximation is sufficiently accurate for orders greater than ½, while at least nine terms might be needed for orders below ¼.

In the above, the simplest algorithm has been used for developing numerical approximations to the differintegral. Other more sophisticated algorithms can be constructed, giving superior convergence properties, or requiring fewer numerical operations, or yielding a higher-order approximation. For example, Oldham and Spanier also give an algorithm in which a Lagrange interpolation is embedded, giving faster convergence. Similarly, various analytic techniques can be used to increase the accuracy of a finite series approximation beyond that obtained by merely truncating the infinite series expressions.

Let I be the image and let S be a mask for I denoting the pixels of the image which are to be included in the analysis. The mask S preferably specifies pixels which are symmetrically distributed around the optical axis of the apparatus. For example, the pixels specified by S may form a circular disk or may form one or more concentric circular annuli, or may form plural segments of such disks or annuli distributed around the optical axis. The mask S may also specify a subset of the pixels in such regions, and the subset may be a patterned subset or a random subset. A convenient method is to multiply a mask defining the contiguous regions with another mask defining the sampling over the whole image. Examples of patterned subsets would be to take odd-numbered pixels in every even-numbered row and even-numbered pixels in every odd-numbered row (one half of the pixels in a checkerboard pattern) or to take alternate pixels in every alternate row of pixels (one fourth of the pixels in a rectangular grid). A random subset may be generated with an arbitrary sampling fraction, and in this case, each selected pixel need not have an exact counterpart pixel in a symmetric position, but the random nature of the sampling ensures statistical symmetry. Thus, the density of the random distribution must be radially symmetric, and is preferably radially uniform, but need not be the same at all distances from the optical axis.

Let us now turn to application of differintegral operators to a digital image. Let $D_x$ be a gradient-type operator in the x direction, and $D_y$ be a corresponding operator in the y direction. The gradient operators are preferably of non-integer order with order between ¼ and ¾. It is advantageous if the gradient-type operators are of the centered type. The gradient-type operators are applied to the image, for instance by convolution:

$$G_x = D_x \otimes I$$

$$G_y = D_y \otimes I \quad (7)$$

where the convolutions are evaluated at each pixel specified in S, producing local gradient estimates in each direction $G_x$ and $G_y$. It is advantageous to combine an averaging operation with the gradient-type operation, such that the gradient value computed for a particular pixel is a weighted average of values computed at plural pixels. It is particularly advantageous if such averaging is performed only in the direction orthogonal to the direction of the gradient-type operator, such that the averaging used in applying operator $D_x$ uses only pixels offset from each other in the y direction, and the averaging used in applying operator $D_y$ uses only pixels offset from each other in the x direction.

Note that considerable computational efficiency can be achieved by implementing the convolution of Eq. 7 using integer arithmetic instead of floating point arithmetic. This is trivial when the convolution kernel terms are differintegral approximations generated from the Grünwald formulation, since Eq. 6 intrinsically yields rational numbers as kernel coefficients if the interval h is unity (when expressed in suitable units), when the differintegral order is itself a rational number. A simple integer scaling then gives whole integer kernel values. Alternatively, an integer-valued kernel can be achieved without changing the units of h by including the factor $h^{-q}$ in the scaling. Similar considerations apply to non-convolution implementations of the gradient-type operation. Integer operations are generally much faster than floating point operations, so that images can be processed more quickly, or can be processed using less sophisticated computational apparatus.

These gradient values in the two directions contain the orientation information of structures at fiber scales in the image. While the directions used for the gradient-type operators need not be orthogonal and need not coincide with the axes of the image, it is advantageous if they are orthogonal and also advantageous if they coincide with the axes of the image, since that maximizes the information content and simplifies subsequent processing, if any. The order of the gradient-type operator can be an integer, such as one (making it a conventional gradient), but it has been have found that the results are more reliable when the order of the gradient-type operator is less than unity, and especially when it is between ¼ and ¾.

Summary information describing the fiber orientation can be extracted from the gradient values in numerous ways. An exemplary method is described here. An orientation angle is assigned to each analyzed pixel as:

$$\theta = \arctan\left(\frac{G_y}{G_x}\right) \tag{8}$$

and an orientation intensity for the pixel is assigned as:

$$J = \sqrt{(G_x)^2 + (G_y)^2} \tag{9}$$

A histogram is then formed, in which a nominal range of angles such as −90° to +90° is divided into plural finite intervals, preferably of equal width, and the orientation intensities are summed for all pixels whose assigned orientation angles are in the same interval, producing a histogram H(θ). This histogram represents the frequency distribution of orientation angles at fiber resolution for the analyzed pixels of the image. This frequency distribution provides a valuable statistical representation of the fiber orientation of the paper. It is a common graphic representation of orientation distributions, often presented as a polar plot of amplitude versus angle, and is employed by some prior art methods of measuring fiber orientation or measuring proxies of fiber orientation, such as tensile stiffness orientation.

The analysis can proceed further by reducing the frequency distribution to a small number of parameters, by fitting it to a standard statistical distribution of suitable form, as is common in said prior art methods. For instance, the histogram can be fitted to a polar parametric form $$H(\theta) = \sqrt{A^2 \cos^2(\theta - \alpha) + B^2 \sin^2(\theta - \alpha)} \tag{10}$$

using least-squares or other methods. An estimate of the average or characteristic fiber orientation is given by the fitted parameter α if A>B, and by α±90° otherwise. The average fiber orientation angle is basically the angle of tilt of the ellipse relative the machine direction. Similarly, if A>B, an estimate of the anisotropy of the fiber orientation distribution is given by:

$$e \sqrt{\frac{A^2 - B^2}{A^2}} \tag{11}$$

in which A and B must be exchanged if B>A. An equivalent formulation of (10) which contains e as a parameter is:

$$H(\theta) = C(1 + e \cos(2\theta - 2\alpha)) \tag{12}$$

If the anisotropy is zero, then there is no characteristic orientation direction. High values of e indicate very strongly oriented sheets with a clearly dominant fiber orientation direction.

Figure 11:
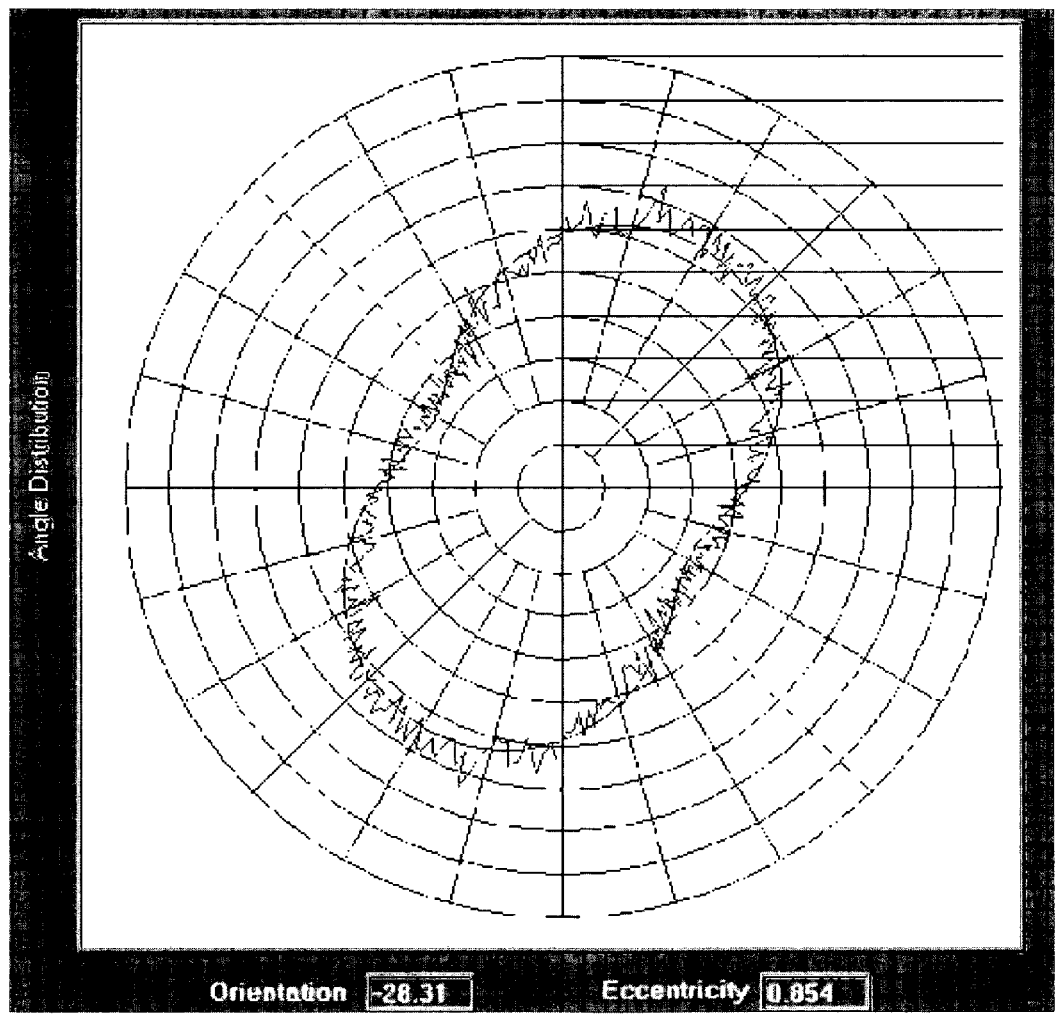
FIG. 11 is an amplitude vs. direction histogram for target pixels.
Figure 12:
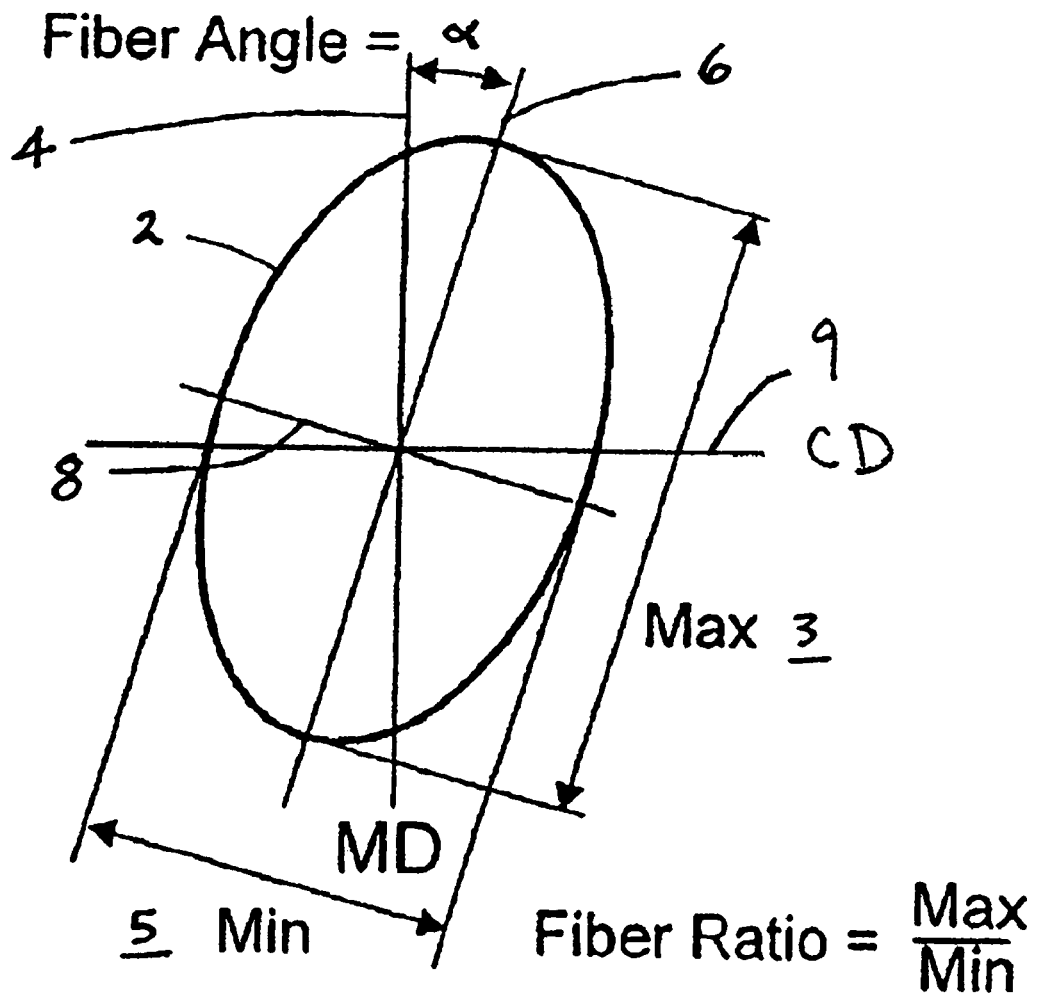
FIG. 12 depicts the definition of fiber orientation measurement.

The fiber orientation anisotropy index is defined in Eq. 11. A is the length of the major axis and B is the length of the minor axis (see FIG. 12). If the sample is isotropic the distribution is a circle, A=B, and e=0. If all the fibers are perfectly aligned, A is large, B~0 and e=1. Finally, statistical fiber orientation is the probability that a fiber is oriented at a particular angle. A sample graph of such is given in FIG. 11 as described herein.

Note that Eq. 10 is by no means the only form suitable for fitting fiber orientation distributions in paper, but is probably the most common. Several other distribution forms can be found in the technical literature, such as K. Schulgasser, "Fibre orientation in machine-made paper", *J. Materials Sci.*, 78, p. 859-866, 1985, or K. J. Niskanen, "Distribution of Fibre Orientation in Paper", *Trans. 9th Fundamental Research Symp. at Cambridge*, vol.1, p. 275-308, September 1989.

While the preferred order of the gradient-type operator is less than unity, the present invention is not confined to such orders, and encompasses use of differintegral operators of arbitrary order in the gradient-type evaluations, including pure integer orders.

The present invention also contemplates use of complex and quaternion order differintegral operators whose order has one or more nonzero imaginary parts. In this case, one or more additional steps can optionally be used to facilitate evaluation of the pixel angle such as in (Eq. 8) and pixel amplitude such as in (Eq. 9). The additional step is to form a suitable norm of a complex or quaternion number, for instance by forming the 2-norm of the value, or by taking its real part, or by forming a norm in a suitable inner-product space, and so forth. As is apparent, norms can be evaluated on a gradient value used in expressions used to compute pixel angle and amplitude such as (Eq. 8) or (Eq. 9), or can be evaluated on the angle and amplitude computed from non-normed values.

Figure 10:
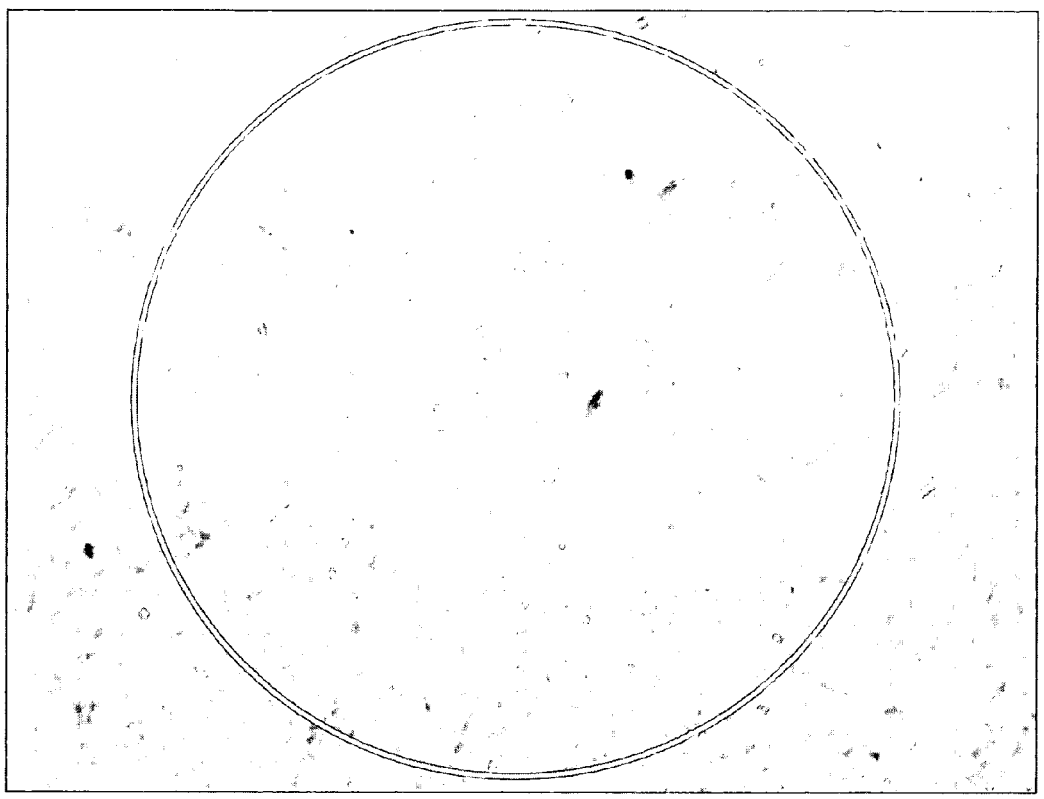
FIG. 10 is a real-time image of browntop linerboard.

Fiber orientation measurements were conducted on linerboard using an apparatus as illustrated in FIG. 6 which included a LED ringlight, a monochrome CCD camera having a pixel scale of approximately 40 microns, and a LED with a strobe speed of 1 microsecond. FIG. 10 depicts a typical real-time image of the moving browntop linerboard from which analysis was conducted. The area for analysis is marked as a circle.

In an exemplary analysis, a random sample of 50% of the pixels in the central disk of the image as shown in FIG. 10 were selected for analysis. At each selected pixel semiderivative operators of order q=½ were applied in the x and y directions (CD and MD) using 7-point symmetric approximation kernels derived from Eq. 6. The resultant gradient vales $D^{1/2}_x$ and $D^{1/2}_y$ were then used to compute the pixel direction=$\tan^{-1}(D^{1/2}_y/D^{1/2}_x)$ and amplitude=$[(D^{1/2}_y)^2+(D^{1/2}_y)^2]^{1/2}$. The amplitude vs. direction histogram for the target pixels is plotted in FIG. 11. The least-squares fit of a parametric form gives the average orientation angle (−28.31°) and the anisotropy expressed as an eccentricity factor (0.854).

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method for measuring the fiber orientation of a moving web, which is formed in a making paper process that comprises the steps of:
   (a) illuminating an area on at least one side of the web with radiation;
   (b) obtaining at least one digital image of the illuminated area, wherein the digital image has an image scale that is sufficient to allow fibers in the moving web to be discerned by employing an imaging detector such that a pixel in the imaging detector corresponds to an image scale which is in the range of from 20 to 40 microns; and
   (c) calculating the fiber orientation of the web by processing at least one digital image with a gradient operator of a non-integer order.

2. The method of claim 1 wherein each image comprises a plurality of pixels and the gradient operator produces a gradient magnitude and direction for at least one of the pixels.

3. The method of claim 1 wherein the gradient operator has a non-integer order of between $\frac{1}{4}$ and $\frac{3}{4}$.

4. The method of claim 1 wherein at least one digital image of the web is acquired on an illuminated side of the web.

5. The method of claim 1 wherein only one side of the web is illuminated and the at least one digital image of the web is acquired on the opposite side of the web where the web is illuminated.

6. The method of claim 1 wherein the fiber orientation is characterized as an average fiber orientation angle.

7. The method of claim 1 wherein the fiber orientation is characterized as a fiber orientation anisotropy index.

8. The method of claim 1 wherein the fiber orientation is characterized as a statistical distribution of fiber orientation angles.

9. The method of claim 1 wherein the fiber orientation is the fiber orientation characteristic of the whole thickness of the web.

10. The method of claim 1 wherein fiber orientation is the fiber orientation characteristic of a surface of the web.

11. The method of claim 10 wherein the fiber orientation is measured for both surfaces of the moving web and the twist and curl deformations of the web, if any, are estimated from the fiber orientation measurements from both surfaces of the web.

12. The method of claim 1 wherein the radiation contains radiation with wavelengths in at least two separate wavelength regions and in step (b) at least two digital images of the illuminated area are acquired substantially simultaneously with the proviso that not all of the images obtained are derived from radiation having the same wavelength and step (c) calculating the fiber orientation of the web by processing the at two digital images with a gradient operator.

13. The method of claim 12 wherein at least one digital image is obtained from each side of the web.

14. The method of claim 1 wherein an image detector is employed in step (b) and step (a) comprises illuminating the area on the web with illumination that is directionally symmetric around an optical axis of the image detector.

15. The method of claim 14 wherein the illumination is provided by a plurality of light sources that are arranged in at least one annulus that is substantially concentric around the optical axis of the image detector.

16. The method of claim 1 further comprising the step of supporting the moving web with a support structure that is located on one side of the web and step (a) comprises illuminating an area on the other side of the web.

17. The method of claim 1 wherein the moving web is non-opaque with respect to the radiation and step (c) includes compensating for radiation that is transmitted through the web and which contain background images.

18. The method of claim 1 wherein the web is a multi-ply web comprising a plurality of plies of web material that are spliced together, wherein the method is further characterized in that:
   (i) the fiber orientation of each of the plurality of plies of web material is measured as each ply is in formed as a moving web; and
   (ii) the fiber orientation measurements made in step (i) are used to characterize the variation in fiber orientation between the plurality of plies of web material of the multi-ply web.

19. The method of claim 1 wherein the moving web comprises a web of paper, paperboard, or tissue.

20. The method of claim 19 wherein the moving web comprises partially drained stock that is being transported on a wire in the forming stage of a manufacturing process.

21. The method of claim 19 wherein the moving web is being supported on a rotating roll at a manufacturing stage that follows a forming stage of a manufacturing process.

22. The method of claim 19 wherein the moving web is being transported on a machine fabric in the pressing or drying stages of a manufacturing process.

23. The method of claim 1 wherein the gradient operator has a non-integer order of between $\frac{1}{3}$ and $\frac{2}{3}$.

* * * * *